(12) United States Patent
Arkles et al.

(10) Patent No.: US 7,790,701 B2
(45) Date of Patent: Sep. 7, 2010

(54) SILICON-BASED TOCOPHEROL DERIVATIVES

(75) Inventors: Barry C. Arkles, Dresher, PA (US); Youlin Pan, Langhorne, PA (US); Jane C. Hollenberg, Redhook, NY (US)

(73) Assignee: Gelest Technologies, Inc., Morrisville, PA (US)

(*) Notice: Subject to any disclaimer, the term of this patent is extended or adjusted under 35 U.S.C. 154(b) by 0 days.

(21) Appl. No.: 11/788,114

(22) Filed: Apr. 19, 2007

(65) Prior Publication Data

US 2007/0253925 A1    Nov. 1, 2007

Related U.S. Application Data

(60) Provisional application No. 60/793,299, filed on Apr. 19, 2006.

(51) Int. Cl.
*A61K 8/89* (2006.01)
*C07F 7/02* (2006.01)

(52) U.S. Cl. ............... 514/63; 549/214; 424/401

(58) Field of Classification Search .......... 514/63; 549/214; 424/401
See application file for complete search history.

(56) References Cited

U.S. PATENT DOCUMENTS

| | | | |
|---|---|---|---|
| 5,466,849 A | 11/1995 | Shioya et al. | |
| 6,261,603 B1 | 7/2001 | McElwain | |
| 6,861,061 B2 | 3/2005 | Maxon et al. | |
| 7,090,862 B2 * | 8/2006 | Barrett-Reis et al. | ........ 424/439 |
| 2005/0008600 A1 | 1/2005 | Nakanishi et al. | |
| 2005/0152864 A1 | 7/2005 | Watanabe et al. | |
| 2006/0024251 A1 | 2/2006 | Gardel et al. | |

FOREIGN PATENT DOCUMENTS

| | | |
|---|---|---|
| EP | 0683164 B1 | 4/1999 |
| WO | WO 2005/102267 A1 | 11/2005 |
| WO | WO 2005/115327 A1 | 12/2005 |

OTHER PUBLICATIONS

Harris, et al. Vitamin E Content of Foods, J. of Nutrition, 40, 1950, 367-381.*
Skinner, et al. Structure-Activity Relations in the Vitamin E Series. II. Derivatives of a-Tocopherol Substituted at the 5-Methyl Group, J. Med. Chem. 12, 1969, 64-66.*
Fiume, Final Report on the Safety Assessment of Tocopherol, Tocopheryl Acetate, Tocopheryl Linoleate, Tocopheryl Linoleate/Oleate, Tocopheryl Nicotinate, Tocopheryl Succinate, Dioleyl Tocopheryl Methylsilanol, Potassium Ascorbyl Tocopheryl Phosphate, and Tocophersolan, International Journal of Toxicology, 21 (suppl. 3) 2002, 51-116.*
Huheey, Inorganic Chemistry Principles of Structure and Reactivity, 4th Edition, HarperCollins College Publishers © 1993, p. 861-863.*
Kira et al. "The First Isolable Dialkylsilylene" J. Am. Chem. Soc. 1999, 121, 9722-9723.*

* cited by examiner

*Primary Examiner*—Sharmila Gollamudi Landau
*Assistant Examiner*—Kortney L Klinkel
(74) *Attorney, Agent, or Firm*—Flaster/Greenberg, P.C.

(57) ABSTRACT

Silicon-based tocopherol derivatives are provided, as well as methods for making the same, in which the derivatives have a tocopherol molecule having a silicon-based group. The derivatives are useful in cosmetic compositions, have antioxidant properties, enhance solubility and compatibility in cosmetic formulations having silicon-based materials within the compositions.

9 Claims, No Drawings

SILICON-BASED TOCOPHEROL DERIVATIVES

CROSS-REFERENCE TO RELATED APPLICATIONS

This application claims the benefit under 35 U.S.C. 119(e) of U.S. Provisional Application No. 60/793,299, filed Apr. 19, 2006 the entire disclosure of which is incorporated herein by reference.

BACKGROUND OF THE INVENTION

α-Tocopherol is a potent source of vitamin E activity. It is one member of a family of structurally related compounds that exhibit biological action. Tocopherols are also found in mixtures of stereoisomers. Vitamin E is the generic descriptive name for all tocopherol and tocotrienol derivatives that act biologically in a manner like α-tocopherol. Tocopherol is the designated name for 2-methyl-2-(4,8,12-trimethyltridecyl)chroman-6-ol as shown below:

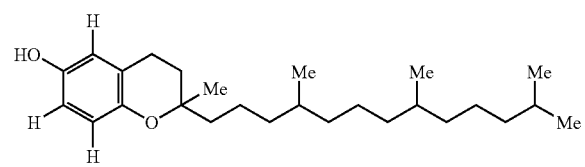

Mono-, di-, and trimethyltocols are known as tocopherols. An α-tocopherol has the structure as noted above but wherein the hydrogens on the hydroxyl-bearing ring are substituted as methyl groups and the compound is a 5,7,8-trimethyltocol:

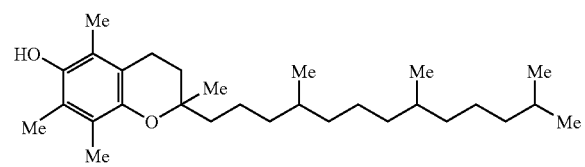

A β-Tocopherol, or 5,8-dimethyltocol has two methyl substitutions as noted below:

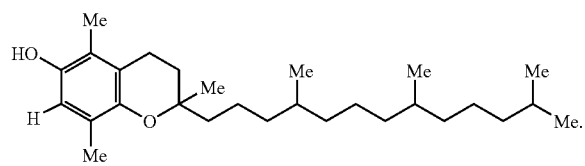

A γ-Tocopherol, or 7,8-dimethyltocol has the following variant structure:

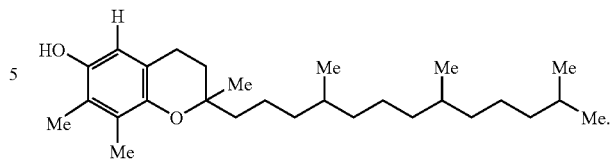

Finally, a δ-tocopherol, or 8-methyltocol has the structure as noted below:

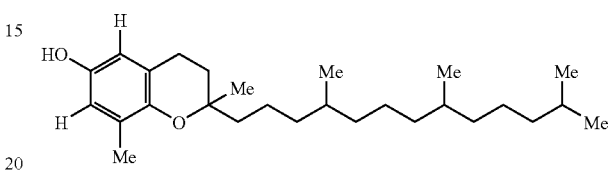

Thus, the Tocopherols generally may be represented by Formula (I) below:

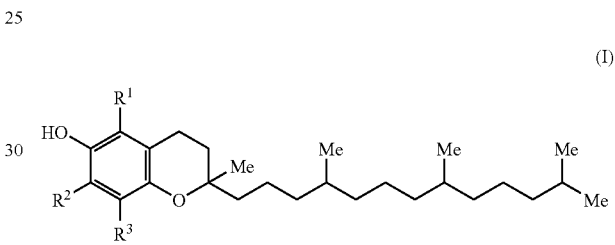

(I)

wherein $R^1$, $R^2$ and $R^3$ are selected from hydrogen and methyl with at least one of the R groups being methyl.

Further variants in the Vitamin E family include those in which the methyl groups on the extending chain are in shifted positions from tocopherol and points of unsaturation appear at the methyl locations forming tocotrienols such as tocotrienol (which is 2-methyl-2-(4,8,12-trimethyltrideca-3,7,11-trienyl)chroman-6-ol), trimethyltocotrienol, dimethyltocotrienol, dimethyltocotrienol and 8-methyltocotrienol.

Tocopherols and tocotrienols are also available in stereoisomeric form and in mixtures of stereoisomers. Thus, there are four known tocopherol and four known tocotrienol isomeric structures, each of which has a chromanol ring with a hydroxyl group and a hydrophobic side chain, which assists in penetration of the compounds into biological membranes.

Tocopherols and tocotrienols react so as to interrupt free radicals and capture the free radicals through the hydroxyl radical and so are generally employed as antioxidants. The hydrogen in the free hydroxyl group acts as a donor to the free radical resulting in a stable free radical form of the initial compound.

Tocopherols and tocotrienols, which are generally referred to in the category of Vitamin E are lipid soluble. It has biological importance for its anti-oxidant capabilities. These compounds are typically used in skin cream and lotions based upon a belief that it encourages skin healing. Thus, it is incorporated into antiaging creams and restorative creams in order to reduce ultraviolet (UV) damage to the skin. Other uses are cosmetic creams such as foundations, gels and lotions, sunscreens and self-tanners.

Vitamin E is available through natural sources (vegetable oils, nuts, sunflower seeds, berries, wheat germ, whole grains, fish, certain vegetables and peanut butter). Most vitamin E in supplement form is derived from vegetable oils such as soybean oil.

Synthetic vitamin E (also known as d,l-tocopherol or d,l tocopheryl acetate) is manufactured as a racemic mixture of alpha tocopherol. Other commercial vitamin Es are available as derivatives from natural sources and are converted into esters from the natural sources using acetic or succinic acid. The tocopherol esters are stabilized and useful in vitamins. Other vitamin E derivatives are esterified for use in cosmetics and pharmaceuticals, including tocopheryl nicotinate ester and tocopheryl linolate ester.

While vitamin E has the above noted uses and properties, it is not always easily solubilized or incorporated into cosmetic formulations. As a result, it is sometimes derivatized as noted above, however, a need still remains in the art for improving compatibility and solubility of vitamin E compounds (tocopherols and tocotrienols) in polymers, such as silicones, commonly used in certain cosmetic and pharmaceutical compositions which will enable the vitamin E compounds to retain their useful properties and beneficial effects.

BRIEF SUMMARY OF THE INVENTION

The invention includes a silicon-based tocopherol derivative comprising a tocopherol molecule having a silicon-based group wherein the silicon based group is bound to the tocopherol molecule on the chromanol group of the tocopherol molecule.

In one embodiment, the invention includes a silicon-based tocopherol derivative wherein the silicon-based group is bound to the tocopherol molecule by way of an oxygen atom in a chromanol ring. This embodiment preferably includes the formation of a silylated alkyl ether (—Si—C—O—) on the tocopherol and the formation of a silylated ether without an intermediate hydrocarbon bridge (—Si—O—) or the formation of a silylated ether without a hydrocarbon bridge (—Si—O—) on the tocopherol, each of which is represented below by a preferred the structure in Formula (V):

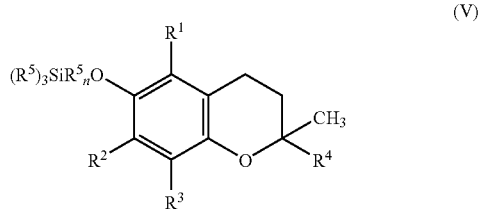

(V)

wherein n=0 or 1, wherein each $R^1$, $R^2$ and $R^3$ is selected from hydrogen and $CH_3$ and at least one of $R^1$, $R^2$ and $R^3$ is $CH_3$;

$R^4$ is $(CH_2CH_2CH_2CH(CH_3))_3CH_3$, $(CH_2CH_2CH=C(CH_3))_3CH_3$ or substituted derivatives thereof;

and each $R^5$ group is independently selected to be a straight or branched chain group of from one to 10 carbon atoms selected from the group consisting of alkyl, alkenyl, alkoxy, alkenoxy, silyl, siloxy, alkylsilyl, alkenylsilyl, alkylsiloxy and alkenylsiloxy or a straight or branched chain silicone polymer which may have one or more oxygen molecules in the chain.

The invention also includes a further embodiment of the silicon based tocopherol derivatives herein wherein a hydroxyl group is positioned ortho or meta to a silicon-based group. This embodiment preferably includes the formation of a silylated alkyl group (e.g., —Si—C—C—) which is positioned ortho or meta to the oxygen (hydroxyl group) having the structure of Formula (VI):

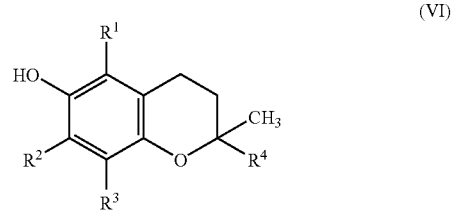

(VI)

wherein each $R^1$, $R^2$ and $R^3$ is selected from hydrogen, —$CH_3$, —$Si(R^6)_p$, —$OSi(R^5)_p$, —$R^5Si(R^5)_p$, or —$R^5OSi(R^5)_p$, wherein at least one of $R^1$, $R^2$ and $R^3$ is —$Si(R^6)_p$, —$OSi(R^5)_p$, —$R^5Si(R^5)_p$ or —$R^5OSi(R^5)_p$, and p is an integer of 1 to 3;

$R^4$ is $(CH_2CH_2CH_2CH(CH_3))_3CH_3$, $(CH_2CH_2CH=C(CH_3))_3CH_3$ or substituted derivatives thereof;

each $R^5$ group is independently selected to be either $R^6$ or, a substituted or unsubstituted, saturated or unsaturated, methyl group;

and each $R^6$ group is independently selected to be hydrogen or a straight or branched chain group of from two to 10 carbon atoms selected from the group consisting of alkyl, alkenyl, alkoxy, alkenoxy, silyl, siloxy, alkylsilyl, alkenylsilyl, alkylsiloxy and alkenylsiloxy or a straight or branched chain silicone polymer which may have one or more oxygen molecules in the chain.

The invention also includes a method for making a silicon-based tocopherol derivative. The method comprises reacting a tocopherol with an allylic halide in a solvent to form an allyloxytocopherol intermediate and reacting the intermediate with a silane compound and a catalyst to form a silicon-based tocopherol derivative.

The invention also includes a cosmetic composition that comprises a cosmetic base formulation and at least one silicon-based tocopherol derivative, comprising a tocopherol molecule having a silicon-based group.

DETAILED DESCRIPTION OF THE INVENTION

This invention describes compositions and methods for preparing silicone-soluble derivatives of tocopherol that are useful for various applications, including formulation into personal care products. The silicone derivatives of tocopherol of the invention are unique hybrid organosilicon compounds formed by attaching tocopherol to a siloxane backbone. The tocopherol substituent adds skin treatment properties to the siloxane backbone while the siloxane component improves the slip and skin feel of the tocopherol. The unique structure enables the organosilicon compounds to act as a solvent for a number of mineral and vegetable waxes.

Preferred embodiments of the compounds of the invention include trisiloxanyl derivatives of tocopherol in which a silane-based group is bound through the hydroxyl groups of the tocopherol molecule and others derivatives wherein the silicon group is/are attached to the chromanol ring of the tocopherol molecule in a position ortho or meta to the hydroxyl group.

Such tocopherol derivatives may be prepared in various ways. In accordance with the one embodiment of the invention, the compounds may be prepared by forming a direct ether linkage between the derivatized group and the phenolic hydroxyl group of tocopherol or by way of forming a hydrocarbon bridge between the phenolic hydroxyl group of tocopherol and the silicon molecule in the silicon-based group. The derivatives herein can also be prepared by forming a direct ether linkage at the position of the hydroxyl group on the tocopherol to form an allyloxy-based intermediate and initiating a rearrangement of the allyloxy group to thereafter attach a silane group to the repositioned allylic group ortho or meta to a "re-formed" hydroxyl group on the chromanol ring of the tocopherol molecule.

These compounds have a broad range of solubility in and compatibility with materials typically used in the formulation of skin care and color cosmetics. They have the additional advantage of being more resistant to becoming rancid or colored during formulation. With respect to certain of the derivatives including a direct —Si—O— bond (i.e., the unbridged derivatives), the phenolic oxygen is directly bound to silicon which allows the tocopherol derivatives of this embodiment to slowly hydrolyze and release free tocopherol which results in reducing dermal inflammation and shows anti-oxidative properties (the structure and method of preparation of the preferred derivatives according to this embodiment are described in EXAMPLE 2 herein).

The bridged derivatives (i.e., those having a silylated alkyl ether (—Si—C—O) bond on the tocopherol ring), while not anti-oxidant, are hydrolytically stable. (The structure and method of preparation of preferred embodiments of these derivatives are described in EXAMPLE 1 herein).

Other preferred derivatives such as those having a silylated alkyl group adjacent to a hydroxy group, for example, and an —Si—C—C— bond on the chromanol ring, are both hydrolytically stable and anti-oxidant in behavior.

Some of the derivatives thereby reduce the tendency of the base tocopherol compounds to become reactive, in theory, by shielding reactive compounds from the oxygen on the chromanol group. Certain of the derivatives (for example, the siloxanyltocopherols) when spread in a thin film on the skin, slowly hydrolyze, liberating tocopherol which have antioxidant activity. Thus, the compounds are storage stable but in use can demonstrate bioactivity.

Unlike many silicones and silicone derivatives, these compounds are easily incorporated into cosmetic products such as skin-care and color cosmetics including lipsticks and foundations due to their solubility in a range of polar compounds such as castor oil and a variety of cosmetic esters. They can also act as co-solvents for tocopherols and silicones. Further, due to such solubility, such derivatives can be useful as a compatibilizer for bioactives, tocopherols, and silicone among other possible applications.

As used herein, the term "tocopherol" is intended to encompass tocopherols, tocotrienols as those compounds are found naturally or synthetically as well as derivatives thereof (including derivatives prepared for use in cosmetic formulations) unless otherwise particularly specified.

The derivatives include a tocopherol molecule, which as noted above may be any of the naturally occurring or synthesized tocopherols or tocotrienols as defined herein having a silicon-based group as a functional group.

Preferred tocopherol derivatives, described herein have a structure in accordance with Formula (V):

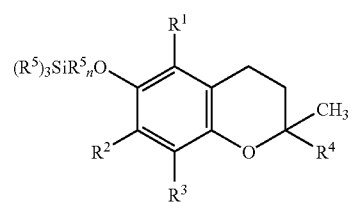

In Formula (V), n=0 or 1, and $R^1$, $R^2$ and $R^3$ are selected from hydrogen and $CH_3$. At least one of $R^1$, $R^2$ and $R^3$ is preferably $CH_3$: $R^4$ in Formula (V) is $(CH_2CH_2CH_2CH(CH_3))_3CH_3$, $(CH_2CH_2CH=C(CH_3))_3CH_3$ or substituted derivatives thereof such that various tocopherol chains are encompassed herein.

Each $R^5$ group is independently selected to be a straight or branched chain group of from one to 10 carbon atoms. Such groups may be alkyl, alkenyl, alkoxy, alkenoxy, silyl, siloxy, alkylsilyl, alkenylsilyl, alkylsiloxy and alkenylsiloxy. It is also within the scope of the invention for $R^5$ group to be various straight or branched chain silicone polymer chains which may have one or more oxygen molecules in the chain. Each $R^1$ $R^2$, $R^3$ and $R^5$ group may be substituted or unsubstituted with various functional groups. Preferred functional groups include but are not limited to amino, sulfonyl, hydroxyl, carbonyl, and halogen.

The silicon-based tocopherol derivatives of this embodiment include a wide variety of derivatized compounds, including most preferred compounds such as, for example, 3-(DL-tocopheroloxypropyl)heptamethyltrisiloxane, 3-(DL-tocopheroloxy)heptamethyltrisiloxane, DL-tocopheroloxypropyltriethoxysilane and DL-tocopheroloxypropyl-terminated polydimethylsiloxane.

While both tocopherols and tocotrienols are encompassed within the scope of the invention, it is preferred that the base molecule herein is a tocopherol derivative such as the mono-, di-, and trimethyltocols noted above in the Background section herein.

The substitution of the phenolic oxygen of the tocopherol in the first embodiment reduces the tendency of the compounds to become rancid. This may be due to inability of the substituted oxygen to intercept radical species and/or could also be due to an increase in the oxygen permeability of the material.

The silicon-based tocopherols of the first embodiment may be prepared by the reaction of a starting compound such as the various tocopherols, tocotrienols and their derivatives as noted above with an allylic halide such as allyl chloride, methallylchloride or allyl bromide to form an allyl ether as an intermediate. The allyl halide reacts with the hydroxyl group of the tocopherol, either in the presence of a base, such as potassium bicarbonate, for example, or by pre-reaction of the hydroxyl group on the tocopherol with a base, for example, sodium amide, sodium hydride or potassium methoxide, to form an allyloxytocopherol intermediate. The intermediate of either of these paths are then reacted with a silane compound and a catalyst to form a silicon-based tocopherol derivative of the original compound by a hydrosilylation reaction.

The silane compounds used in the reaction may be any of a wide variety of silicon-based compounds, and preferably include alkylsilanes, alkoxysilanes, alkylsiloxanes and alkoxysiloxanes and their derivatized or functionalized counterparts. Examples include, without limitation, bis(trimethylsiloxy)methylsilane, bis(trimethylsiloxy)ethylsilane, bis(trimethylsiloxy)propylsilane, bis(triethylsiloxy)methylsilane, bis(triethylsiloxy)ethylsilane, bis(triethylsiloxy)propylsilane, triethoxysilane, trimethoxysilane, tripropylsilane, bis(tripropylsiloxy)methylsilane, bis(tripropylsiloxy)ethylsilane, bis(tripropylsiloxy)propylsilane and similar compounds as well as their functionalized derivatives having functional groups such as those noted above with respect to Formula (V) and the $R^5$ group.

Other preferred silicon-based tocopherol derivatives according to the invention maintain a hydroxyl group positioned ortho or meta to a silicon based group on the chromanol group. Such silicon-based tocopherol derivatives preferably have the structure of Formula (VI):

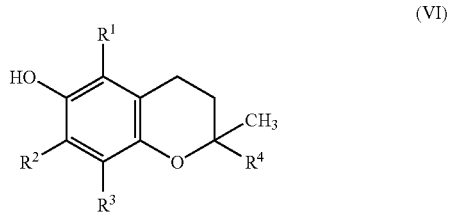

(VI)

In Formula (VI), $R^1$, $R^2$ and $R^3$ may independently be chosen as hydrogen, —$CH_3$, —$Si(R^6)_p$, —$OSi(R^5)_p$, —$R^5Si(R^5)_p$, or —$R^5OSi(R^5)_p$, but preferably at least one of $R^1$, $R^2$ and $R^3$ is —$Si(R^6)_p$, —$OSi(R^5)_p$, —$R^5Si(R^5)_p$ or —$R^5OSi(R^5)_p$. It is preferred also that p is an integer of 1 to 3. As with Formula (V), $R^4$ may be $(CH_2CH_2CH_2CH(CH_3))_3CH_3$, $(CH_2CH_2CH=C(CH_3))_3CH_3$ or substituted derivatives thereof.

Each $R^5$ group may differ and can be either $R^6$ or, a substituted or unsubstituted, saturated or unsaturated methyl group. Further, each $R^6$ group may vary and may be hydrogen or a straight or branched chain group of from two to 10 carbon atoms. Preferred groups include alkyl, alkenyl, alkoxy, alkenoxy, silyl, siloxy, alkylsilyl, alkenylsilyl, alkylsiloxy and alkenylsiloxy, as with Formula (V), $R^6$ may include a straight or branched chain silicone polymer which may have one or more oxygen molecules in the chain, wherein each of the $R^1$, $R^2$, $R^3$, $R^5$, and $R^6$ groups may be substituted with functional groups. Such groups include but are not limited to amino, sulfonyl, hydroxyl, carbonyl, and halogen.

The silicon based tocopherol derivative according to this embodiment can include a variety of compounds including the preferred compounds; 5-bis(trimethylsiloxy)methylsilylpropyl-7-methyl-α-tocopherol and 5-methyl-7-bis(trimethylsiloxy)methylsilylpropyl-α-tocopherol.

One advantage of this embodiment is that the siloxane-modified tocopherol derivatives exhibit biological activity but are stabilized by the siloxane and capable of being readily formulated into cosmetic formulations.

In making the silicon-based tocopherol derivatives such as those in Formula (VI), the base compound such as the various tocopherols, tocotrienols and their derivatives as noted herein are reacted with an allylhalide in a solvent to form an allyloxytocopherol as an intermediate preferably ether using an initial base reaction or in the presence of a base. Preferably tocopherols are selected so as to maximize the β- and γ- and δ-tocopherols as well as α-tocopherol. The intermediate is then preferably subjected to a rearrangement, such as a Claisen rearrangement, prior to reacting the intermediate with a silane compound and a catalyst. Preferably, the compound is heated to allow rearrangement to occur. Rearrangement may be done through other methods as well. After rearrangement, the intermediate is replaced with a silane compound, such as those noted above to form a silicon-based tocopherol derivative wherein the silane group is positioned ortho or meta to a non-displaced hydroxyl group on the chromanol group of the tocopherol molecule.

Also useful as a silane compound herein are polymeric silicon-containing molecules having similar reactive capabilities as the silane monomeric structures noted above, such as polydimethylsiloxane, polydiethylsiloxane, polydipropylsiloxane, polymethylethylsilane, polymethylpropylsiloxane, and other polyalkyl- or polyalkenyl-siloxanes as are known in the art or to be developed. Chain lengths may vary, but it is preferred that the molecular weight (Mn) of polymeric silane compounds used to form polymeric silicon-based derivative groups on tocopherol be from 100 to about 5000, and most preferably from about 500 to about 2000. It should be noted that variations in molecular weight above and below this range are within the scope of the invention and that the components having different chain lengths can contribute varying properties accordingly. For example, generally, lower molecular weight chains would tend to be more emollient in nature while higher molecular weight chains would tend to be more substantive in terms of being longer-wearing on skin and more resistant to wash-off.

The base reactions for forming derivatives herein are preferably carried out initially in a solvent environment with agitation such as stirring to facilitate reaction. The initial reactants, a base such as sodium amide and an allyl halide such as allylbromide, are preferably added sequentially and the reaction allowed to proceed to form the intermediate. Volatiles, such as any ammonia or other byproducts are preferably removed before reacting the resulting intermediate with the silane compound.

In forming a derivative such as that of Formula (VI), once the allyl ether is attached replacing the hydrogen atom of the hydroxyl group, the compound is rearranged, such as by heating so as to move the allyl group of the oxygen atom. After the intermediate is formed and optionally rearranged, the intermediate is reacted with the silane compound as discussed above. This preferably proceeds by adding the reactant silane compound in a partial portion to initiate the reaction followed by introduction of at least some of a reaction catalyst, such as a Pt content Karstedt catalyst (see U.S. Pat. No. 3,775,452, which is incorporated herein by reference in relevant part) or chloroplatinic acid. After initiation, the remaining reactants and catalyst are added and the reaction allowed to proceed to form the resulting silicon-based tocopherol derivative.

The silicon-based tocopherols described herein may be used in various cosmetic compositions, including preferably those which have silicon compounds or silicone based polymers in the base formulation, since the derivatives facilitate compatibility and solubility in such compounds within formulations, but the invention is not limited to those cosmetic compositions and may include any cosmetic composition in which the silicon-based tocopherol derivatives are useful. The cosmetic compositions of the present invention include a cosmetic base formulation, which may be any suitable cosmetic base formulation and at least one silicon-based tocopherol derivative as described herein. The silicon-based tocopherol derivatives include a tocopherol molecule or a commercial or natural derivative thereof and include a silicon-based group bonded to the tocopherol molecule (or the derivative thereof) by way of the chromanol group, more particularly through the oxygen atom in the chromanol ring in the tocopherol molecule or in a position ortho or meta to hydroxyl group on the chromanol ring.

Typical cosmetic base formulations for use with the silicon-based tocopherol derivatives described herein in the cosmetic compositions within the invention include, without limitation creams, lotions, sunscreens, lipsticks, cream eyeshadows, blush, antiaging creams, sunburn creams, self-tanning lotions, foundation and hair cosmetics.

When incorporated in such formulations, it is preferred that the silicon-based tocopherol derivative is present in an amount of about 0.01 percent by weight to about 20 percent by weight, preferably about 1 percent by weight to about 10 weight percent and most preferably about 1 to about 5 percent by weight based on the weight of the formulation.

If a silicon compound or silicone polymer is used in the formulation, it may include compounds or polymers such as organopolysiloxane polymers or cross-linked elastomers as are known in the art or to be developed. However, other polymer base materials may also be used in the base formulation, whether natural or synthetic, including sodium alginate, carrageen, agar, furcelleran, guar gum, methyl cellulose, ethyl cellulose, hydroxypropyl cellulose, carboxymethyl cellulose, starch and starch derivatives, albumin, casein, gelatin, polyacrylates and salts thereof, polyacrylic amides, carboxyvinyl polymers, polyethylene imines, polyethylene glycol, polyols, polyether polyols, polyvinyl alcohols, polyvinyl pyrrolidones, polyvinyl ethers, polyacrylic acids, polymethacrylic acids, maleic acid polymers, polyamides, and the like.

Other components for use in the cosmetic base formulation include, but are not limited to, metal oxides, polyolefins, sunscreen active agents such as UVA and/or UVB absorbing materials (organic and inorganic); oils such as silicone oils, oil emulsions (water-in-oil, water-in-silicone, combinations thereof); natural fats, fatty acids, fatty oils and alcohols (avocado oil, almond oil, olive oil, sesame seed oil, rice oil, corn oil, safflower oil, soybean oil, rape seed oil, palm oil, caster oil, high oleic sunflower oil, coconut oil, tallow oil, meadowfoam and similar compounds, lauric acid, myristic acid, stearic acid, isostearic acid, triisostearic acid, behenic acid, oleic acid, isostearyl citrate, triisostearyl citrate, glyceryl stearate, sorbitan stearate, ocyldocecyl stearate, linoleic acid, cetyl alcohol, isostearyl alcohol, ceteareth, ceteareth alcohol, decanol, octyldodecanol); waxes (jojoba oil, canauba wax, candelilla wax, rice bran wax, lanolin, beeswax, montan wax, microcrystalline wax, ceresin and similar waxes), emulsifiers and base formulators (including surfactants and emulsifiers of the non-ionic, anionic, cationic, zwitterionic and amphoteric, parabens, methylparabens, propylparabens, and polymeric materials such as polyoxyalkylene polymers and copolymers, polyethers, polyether polyols, polyglycols, polyalkylene glycols, polyglycerins, polydimethicones and similar polymers and mixtures, combinations and copolymers thereof); saccharides (mannitol, sylitol, sorbitol, pentaerythritol, erythritol, glucose, sucrose, fructose, lactose and the like) and additives such as microspheres, humectants, exfoliants, emollients, gelling agents, amino acids, enzymes and peptides, proteins, polysorbates, alkylamines, other vitamin and vitamin derivatives, including other tocopherols, tocotrienols and derivatives thereof, anti-acne components, flavonoids, EDTA and salts thereof, skin soothing agents, fragrances, colorants (pigments and dyes in various color combinations whether natural or synthetic, metallic oxides), herbal components and extracts, natural or synthetic oils, mica, talc and other similar fillers, antioxidants, chelators, antifungals, antibacterial agents, antimicrobial agents, antiseptics and medicaments. The amounts and ratios of these components may vary in accordance with the nature of the formulation or intended use of the cosmetic formulation and the components and amounts thereof are not intended to be limited herein.

Natural and natural derivative therapeutics and preventatives are an important healthcare products which are effective in combating many maladies. The antioxidant compounds of the present invention are an important contribution of the molecules as they represent a stable compound for distribution prior to application/use and an important healthcare product.

Example 1

3-(DL-Tocopheroloxypropyl)heptamethyltrisiloxane was synthesized as follows:

A 22 liter, 4-neck flask equipped with heating mantle, mechanical stirrer, pot thermometer, dry-ice condenser and an addition funnel was charged with 409.6 g of sodium amide and 5 l of toluene. Agitation was initiated and 4307.2 g of tocopherol were added over two hours at a rate to maintain pot temperature below 70° C. After the addition was complete, the reaction mixture was maintained at 70° C. for an additional 2 hours during which time the evolution of ammonia stopped. Allylbromide (1209.8 g) was added over a period of 1 hour. The mixture was then heated at 85-95° C. for 16 hours. The mixture was allowed to cool to room temperature. To the mixture was added 5 l of water. The organic (top) layer was separated from the water layer and then washed 2 times with 10 l of water. The organic layer was separated and dried over anhydrous sodium sulfate overnight. Most of the toluene was then removed by distillation, maintaining pot temperature below 140° C. The remaining volatile components were removed by vacuum distillation at 2 mm Hg with a maximum pot temperature of 80° C. to give allyloxy-DL-tocopherol, a clear dark amber viscous liquid (4.23 kg) of sufficient quality for the next reaction step. If desired, this intermediate can be purified by distillation at 220-250° C. at 0.1 mm Hg.

A 12 liter, 3-neck flask equipped with heating mantle, mechanical stirrer, pot thermometer, condenser and addition funnel was charged with 4001.6 g of allyloxytocopherol. With agitation the flask was heated to 80-90° C. and then heating was stopped. 100 mls of bis(trimethylsiloxy)methylsilane were added followed by 2 ml of 2% Pt content Karstedt catalyst. After initiation was observed, the balance of the bis(trimethylsiloxy)methylsilane was added at a rate to maintain pot temperature at 85-115° C. During the course of the addition, 1 ml of catalyst was added. After the addition was complete, a final 1 ml of catalyst was added and the mixture was heated to 90° C. for 2 h. The mixture was allowed to cool below 50° C., and 2 l of hexane were added. The mixture was washed with two 3 l portions of 6% aqueous sodium hypochlorite, then with two 6 l portions of distilled water and then dried over anhydrous sodium sulfate. The reaction mixture was then stripped at 120° C. at 0.5 mmHg to yield a yellow liquid with a very mild odor that was identified by FTIR and NMR as 3-(DL-Tocopheroloxypropyl)heptamethyltrisiloxane with the following physical properties-$D_4^{20}$: 0.922, $n_o^{20}$: 1.4274, viscosity, 25°: 625 cSt. The compound has the following structure:

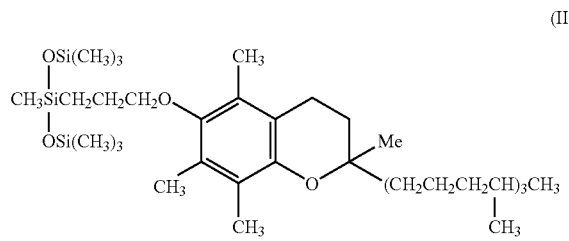

(II)

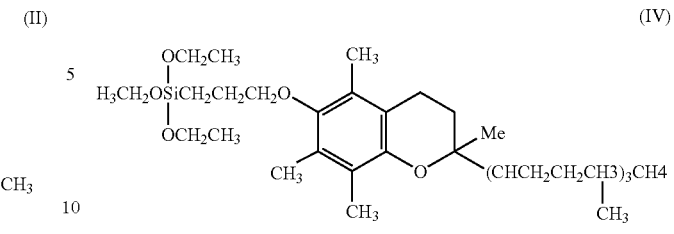

(IV)

Example 2

3-(DL-Tocopheroloxy)heptamethyltrisiloxane was synthesized by the direct reaction of tocopherol and heptamethyltrisiloxane in the presence of a Karstedt catalyst by a dehydrogenated coupling reaction. A dry, 2 L 4-neck flask equipped with a mechanical stirrer, pot thermometer, dry-ice condenser and an addition funnel was charged with 222.5 g of bis(trimethylsiloxy)methylsilane and 2.5 ml of a 5 Pt % chloroplatinic acid solution in tetrahydrofuran and heated to 100-120° C.; 430.7 g of α-tocopherol was then added. The mixture was heated at 120-140° C. for 16 hours during which time the evolution of hydrogen ceased. The mixture was cooled to room temperature, wherein 750 ml of heptane were added. The mixture was warmed to 40° C. and filtered through silica gel to remove platinum, and then stripped at 120° C. at 0.5 mm Hg to give 610 g of deep amber liquid. FTIR was consistent with <3% free hydroxyl and consistent with the proposed structure.

The compound formed had the following structure:

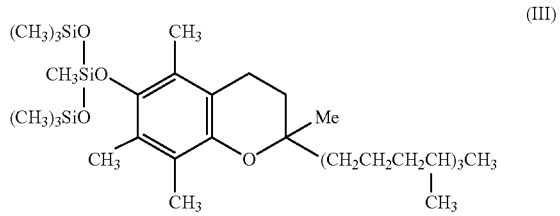

(III)

Example 3

Formation of DL-Tocopheroloxypropyltriethoxysilane:

A one liter, 3-neck flask equipped with magnetic stirrer, pot thermometer, dry-ice condenser and an addition funnel was charged with 117.7 g of allyloxytocopherol and 100 ml of toluene. The mixture was heated to 80-90° C. and 20 g of triethoxysilane were added followed by 0.5 g of Pt complex. After the initial exotherm subsided, the balance of 23.1 g of triethoxysilane was added at a pot temperature of 85-115° C. After the addition of triethoxysilane was complete, a further portion of 0.5 ml of Pt complex was added and the mixture heated to 90° C. for 1 hour. Activated carbon (5 g) was then added to the mixture maintaining agitation and a pot temperature of 30-40° C. for 2-3 hours. The mixture was then filtered and stripped at 100° C. at 1 mmHg to yield 128.8 g product, 82% yield. $D_4^{20}$: 0.956 g/ml, $n_o^{20}$: 1.485. NMR was consistent with proposed structure:

Example 4

Formation of DL-Tocopheroloxypropyl-terminated Polydimethylsiloxane:

A 2 liter, 3 neck flask equipped with magnetic stirrer, pot thermometer, dry-ice condenser and an addition funnel was charged with 141.2 g of allyloxytocopherol and 300 ml of toluene. After heating to 80-90° C., 30 g of hydride-terminated polydimethylsiloxane (Mn: 1050) was added followed by 0.5 ml of Karstedt Pt complex in xylene. Once initiation was observed and exotherm subsided, the balance of 127.5 g of hydride-terminated polydimethylsiloxane was added at a pot temperature at 85°-115° C. After the addition was complete, the mixture was heated to 90° for 2 hours. FTIR indicated that all Si—H was consumed. Activated charcoal, 20 g, was added to the mixture and stirred overnight. The mixture was filtered and then stripped under 1 mm vacuum to a maximum pot temperature of 80° C. NMR was consistent with the proposed structure at about 95% purity. $D_4^{20}$: 0.947 g/ml; $n_o^{20}$: 1.4564; viscosity 725 centistokes.

Example 5

Under similar conditions to those of Example 4, a hydride-terminated PDMSO (Mn: 450) was reacted with allyloxytocopherol. A product was produced with $D_4^{20}$: 0.945 g/ml; $n_o^{20}$: 1.4762; viscosity 525 centistokes.

Example 6

Lipstick Formulation: The color-grind was prepared in advance using a three-roll mill. The three waxes, oils and preservatives were combined and then heated to 85-87° C. and stirred until clear. The color-grind and mica were added and stirred until homogeneous a homogeneous mixture formed. The mixture having the components noted below in Table 1 were then cooled to 72° and filled into molds.

TABLE 1

| Ingredient (INCI Name) | Weight Percentage |
|---|---|
| Crystal O, Caschem (castor Oil) | 14.38 |
| Schercemol TISC (triisostearyl citrate) | 30.00 |
| Eutanol G (octyldodecanol) | 6.00 |
| 3-(DL-Tocopheroloxypropyl)heptamethyltrisiloxane | 10.00 |
| Methylparaben | 0.20 |
| Propylparaben | 0.10 |
| Candelilla | 7.00 |
| Microwax SP 19, Strahl & Pitch (microcrystalline wax) | 3.50 |
| Ozokerite 170D, Ross Wax (ceresin) | 2.00 |
| Carnauba | 1.50 |

TABLE 1-continued

| Ingredient (INCI Name) | Weight Percentage |
|---|---|
| Color Grind | |
| Crystal O | 7.75 |
| A-1206, Color Techniques (iron oxides) | 6.00 |
| X-200, Kemira (titanium dioxide) | 1.70 |
| A-1301, Color Techniques (iron oxides) | 1.70 |
| C19-7711, Sun Red 7 Lake | 0.17 |
| Mearlmica CF, Englehard (mica) | 8.00 |
| Total | 100.00 |

Example 7

An Oil in Water emulsion was prepared as follows according to Table 2:

TABLE 2

| | Ingredient (INCI Name) | Weight Percentage |
|---|---|---|
| Part A | Deionized Water | 71.15 |
| Part A | Ultrez 10 (Carbomer) | 0.20 |
| Part A | Butylene Glycol | 4.00 |
| Part A | Methylparaben | 0.30 |
| Part A | Tween 60 (Polysorbate 60) | 0.50 |
| Phase B | TRIS Amino (Trimethamine) | |
| Phase B | Deionized Water | 3.0 |
| Part C | Disodium EDTA | 0.05 |
| Oil Phase D | Emersol 132 (Stearic Acid) | 2.00 |
| Oil Phase D | Cerasynt SD (Glyceryl Stearate) | 1.00 |
| Oil Phase D | Arlacel 60 (Sorbitan Stearate) | 0.50 |
| Oil Phase D | Ceraphyl ODS (Octyldodecyl Stearate) | 9.00 |
| Oil Phase D | 3-(DL-Tocopheroloxypropyl)heptamethyltrisiloxane | 6.00 |
| Oil Phase D | Propylparaben | 0.10 |
| Part E | Germall II (diazolidinyl urea) | 0.20 |
| Part E | Deionized Water | 1.00 |

In Part A, Ultrez was added to water while homogenizing. It was heated to 75° C. Then the remaining ingredients were added in order. Phase B was combined and added to Part A. Then Part C was added. In a separate vessel, Oil Phase D was combined. It was heated to 75-80° C. while stirring. Part D was added to combined Part A, Phase B and Part C while homogenizing. The temperature and homogenization were maintained for 15 minutes. The formulation was cooled to 45° C. with paddle agitation. Part E was then combined and added. The formulation was cooled to 30° C. and the batch packaged.

Example 8

Allyloxy tocopherol was prepared from a natural product-derived mixture of tocopherols containing high β-tocopherol and γ-tocopherol in addition to α-tocopherol. A commercial sample of Archer Daniels Midland Decanox mixed Tocopherols MTS-90 which contains 90% mixed tocopherols, ~10% inactives and ~20% α-tocopherol, with the balance primarily β-, γ- and, δ-tocopherols was used. 0.25M (114 g) of the allyl ether prepared according to EXAMPLE 1 was charged to a 500 ml flask equipped with a magnetic stirrer condenser. The heating mantle was heated under nitrogen for 3 hours at 200-225° C. and allowed to cool. Products of a Claisen rearrangement were evident as indicated by a free phenolic hydroxyl group demonstrated by the relative increase in —OH absorption observed by FTIR and allyl substituted aromatic positions observed by NMR. The mixture was warmed to 80-90° C. and 10 g of bis(trimethylsiloxy) silane was added followed by 0.1 ml of Karstedt catalyst. After the exotherm subsided, an additional 54 g of bis(trimethylsiloxy)silane was added followed by an additional 0.1 ml of Karstedt catalyst. The mixture was heated to 90° C. for 2 hours. The product mixture was filtered through silica to remove residual platinum and then stripped under vacuum to yield a mixture that consisted primarily of 5-bis(trimethylsiloxy)methylsilylpropyl-7-methyl-α-tocopherol, 5-methyl-7-bis(trimethylsiloxy)methylsilylpropyl-α-tocopherol and the corresponding bis(trimethylsiloxy)silylethers of the 6-hydroxyl group as well as the product of EXAMPLE 2, 3-(DL-α-tocopheroloxy)heptamethyltrisiloxane. The 6 hydroxyl group was disilylated by adding 5 ml of concentrated HCl, 50 ml ethanol and 50 ml of water and heating with agitation to 80° C. for 4-6 hours. The product mixture was stripped at 100-120° C. at less than 1 mm vacuum. The amber liquid indicated a structure by NMR and IR consistent with an isomeric mixture of methyl[bis(trimethylsiloxy)methylsilylpropyl]tocopherols.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A silicon-based tocopherol derivative represented by the formula V and by the formula VI, wherein the structure of formula (V) is:

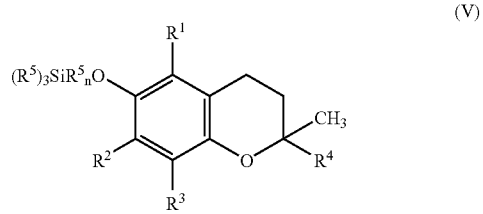

wherein n=0 or 1, wherein each of $R^1$, $R^2$ and $R^3$ are selected from hydrogen and $CH_3$ and at least one of $R^1$, $R^2$ and $R^3$ is $CH_3$;

$R^4$ is $(CH_2CH_2CH_2CH(CH_3))_3CH_3$, or $(CH_2CH_2CH=C(CH_3))_3CH_3$; and each $R^5$ group is independently selected to be a straight or branched chain group of from one to 10 carbon atoms selected from the group consisting of alkyl, alkenyl, alkoxy, alkenoxy, silyl, siloxy, alkylsilyl, alkenylsilyl, alkylsiloxy and alkenylsiloxy or a straight or branched chain silicone polymer which may have one or more oxygen molecules in the chain; and the structure of formula VI is:

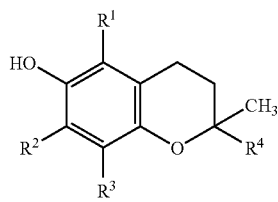

wherein $R^1$, $R^2$ and $R^3$ are independently selected from hydrogen, —$CH_3$, —$Si(R^6)_p$, —$OSi(R^5)_p$, —$R^5Si(R^5)_p$, and —$R^5OSi(R^5)_p$, wherein at least one of $R^1$, $R^2$ and $R^3$ is —$Si(R^6)_p$, —$OSi(R^5)_p$, —$R^5Si(R^5)_p$ or —$R^5OSi(R^5)_p$, and p is 3; $R^4$ is $(CH_2CH_2CH_2CH(CH_3))_3CH_3$ or $(CH_2CH_2CH=C(CH_3))_3CH_3$; each $R^5$ group is independently selected to be either $R^6$ or, a substituted or unsubstituted, saturated or unsaturated, methyl group; and each $R^6$ group is independently selected to be hydrogen or a straight or branched chain group of from two to 10 carbon atoms selected from the group consisting of alkyl, alkenyl, alkoxy, alkenoxy, silyl, siloxy, alkylsilyl, alkenylsilyl, alkylsiloxy and alkenylsiloxy or a straight or branched chain silicone polymer which may have one or more oxygen molecules in the chain.

2. The silicon-based tocopherol derivative according to claim 1, wherein the compound remains chemically stable until exposed to hydrolysis upon application to the skin wherein the tocopherols which act as antioxidants are liberated.

3. The silicon-based tocopherol derivative according to claim 1, wherein the derivative is selected from the group consisting of 3-(DL-tocopheroloxypropyl)heptamethyltrisiloxane, 3-(DL-tocopheroloxy)heptamethyltrisiloxane, DL-tocopheroloxypropyltriethoxysilane, and DL-tocopheroloxypropyl-terminated polydimethylsiloxane.

4. The silicon-based tocopherol derivative according to claim 1, wherein the derivative is selected from the group consisting of 5-bis(trimethylsiloxy)methylsilylpropyl-7-methyl-α-tocopherol and 5-methyl-7-bis(trimethylsiloxy)methylsilylpropyl-α-tocopherol.

5. A cosmetic composition comprising:
a cosmetic base formulation, and
at least one silicon-based tocopherol derivative represented by the formula V and by the formula VI, wherein:
the structure of formula (V) is:

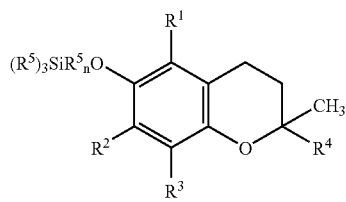

wherein n=0 or 1, wherein each of $R^1$, $R^2$ and $R^3$ are selected from hydrogen and $CH_3$ and at least one of $R^1$, $R^2$ and $R^3$ is $CH_3$;
$R^4$ is $(CH_2CH_2CH_2CH(CH_3))_3CH_3$, or $(CH_2CH_2CH=C(CH_3))_3CH_3$; and each $R^5$ group is independently selected to be a straight or branched chain group of from one to 10 carbon atoms selected from the group consisting of alkyl, alkenyl, alkoxy, alkenoxy, silyl, siloxy, alkylsilyl, alkenylsilyl, alkylsiloxy and alkenylsiloxy or a straight or branched chain silicone polymer which may have one or more oxygen molecules in the chain; and the structure of formula VI is:

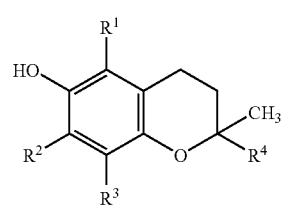

wherein $R^1$, $R^2$ and $R^3$ are independently selected from hydrogen, —$CH_3$, —$Si(R^6)_p$, —$OSi(R^5)_p$, —$R^5Si(R^5)_p$, and —$R^5OSi(R^5)_p$, wherein at least one of $R^1$, $R^2$ and $R^3$ is —$Si(R^6)_p$, —$OSi(R^5)_p$, —$R^5Si(R^5)_p$ or —$R^5OSi(R^5)_p$, and p is 3; $R^4$ is $(CH_2CH_2CH_2CH(CH_3))_3CH_3$ or $(CH_2CH_2CH=C(CH_3))_3CH_3$; each $R^5$ group is independently selected to be either $R^6$ or, a substituted or unsubstituted, saturated or unsaturated, methyl group; and each $R^6$ group is independently selected to be hydrogen or a straight or branched chain group of from two to 10 carbon atoms selected from the group consisting of alkyl, alkenyl, alkoxy, alkenoxy, silyl, siloxy, alkylsilyl, alkenylsilyl, alkylsiloxy and alkenylsiloxy or a straight or branched chain silicone polymer which may have one or more oxygen molecules in the chain.

6. The cosmetic composition according to claim 5, wherein the silicon-based tocopherol is selected from the group consisting of 3-(DL-tocopheroloxypropyl)heptamethyltrisiloxane, 3-(DL-tocopheroloxy)heptamethyltrisiloxane, DL-tocopheroloxypropyltriethoxysilane, and DL-tocopheroloxypropyl-terminated polydimethylsiloxane.

7. The cosmetic formulation according to claim 5, wherein the formulation is selected from the group consisting of creams, lotions, sunscreens, lipsticks, cream eyeshadows, blush, antiaging creams, sunburn creams, self-tanning lotions, foundation and hair cosmetics.

8. The cosmetic formulation according to claim 5, wherein the cosmetic base formulation comprises a silicone polymer or a silane-based compound.

9. The cosmetic composition according to claim 5, wherein the silicon-based tocopherol derivative is selected from the group consisting of 5-bis(trimethylsiloxy)methylsilylpropyl-7-methyl-α-tocopherol and 5-methyl-7-bis(trimethylsiloxy)methylsilylpropyl-α-tocopherol.

\* \* \* \* \*